(12) United States Patent
Enge

(10) Patent No.: US 11,400,228 B2
(45) Date of Patent: Aug. 2, 2022

(54) MEDICAMENT DELIVERY DEVICE

(71) Applicant: Carebay Europe Ltd., Sliema (MT)

(72) Inventor: Kasper Enge, Järfälla (SE)

(73) Assignee: SHL MEDICAL AG, Zug (CH)

( * ) Notice: Subject to any disclaimer, the term of this patent is extended or adjusted under 35 U.S.C. 154(b) by 1066 days.

(21) Appl. No.: 16/067,434

(22) PCT Filed: Nov. 16, 2016

(86) PCT No.: PCT/EP2016/077879
§ 371 (c)(1),
(2) Date: Jun. 29, 2018

(87) PCT Pub. No.: WO2017/114612
PCT Pub. Date: Jul. 6, 2017

(65) Prior Publication Data
US 2019/0022329 A1    Jan. 24, 2019

(30) Foreign Application Priority Data
Dec. 30, 2015  (SE) .................................. 1551721-2

(51) Int. Cl.
*A61M 5/315*          (2006.01)
*A61M 5/24*           (2006.01)
(Continued)

(52) U.S. Cl.
CPC ...... *A61M 5/31551* (2013.01); *A61M 5/2033* (2013.01); *A61M 5/24* (2013.01);
(Continued)

(58) Field of Classification Search
CPC .. A61M 5/31551; A61M 5/2033; A61M 5/24; A61M 5/2422; A61M 5/31536;
(Continued)

(56) References Cited

U.S. PATENT DOCUMENTS 5,112,317 A * 5/1992 Michel .................... A61M 5/24
222/386
5,226,896 A * 7/1993 Harris ................. A61M 5/5013
604/211

(Continued)

FOREIGN PATENT DOCUMENTS

WO    2006130098 A1    12/2006
WO    2014029725 A1    2/2014
WO    2016139023 A1    9/2016

*Primary Examiner* — Dung T Ulsh
(74) *Attorney, Agent, or Firm* — McDonnell Boehnen Hulbert & Berghoff LLP

(57) ABSTRACT

The present invention relates to a medicament delivery device (10) comprising a housing (12, 14); a medicament container holder (90), arranged movable in relation to said housing (12, 14) and capable of accommodating a medicament container (92); an biased activator (160) comprising a plunger rod (164), which plunger rod (164) is arranged to act on the medicament container (92) for delivering a dose of medicament through a medicament delivery member (102 when said biased activator (160) is operated; a manually operable dose setting member (72) operably connected to both said housing and said medicament container holder such that manual operation of said dose setting member (72) will cause the medicament container holder (90) with the medicament container (92) to move towards said plunger rod (164) for setting a dose of medicament to be delivered; a dose drum (56) releasably connected to the dose setting member (72) through a releasable connection mechanism (68, 84I) such that when the dose setting member is operated, said dose drum (56) is displaced from an initial position to a set dose position; a release mechanism (116) operably connected to said biased activator (160), wherein, when said plunger rod (164) is moved to an end position of the dose delivery operation, said release mechanism (116) is arranged to act on said connection mechanism (68, 84I) for (Continued)

releasing said dose drum (56) from said dose setting member (72). The invention is characterised in that said release mechanism is arranged with a locking mechanism (130, 84II) arranged to lock said dose setting member (72) from displacement as the connection mechanism (68, 84I) is operated for releasing said dose drum (56) from said dose setting member (72).

20 Claims, 17 Drawing Sheets

(51) Int. Cl.
*A61M 5/20* (2006.01)
*A61M 5/31* (2006.01)
(52) U.S. Cl.
CPC ........ *A61M 5/2422* (2013.01); *A61M 5/3158* (2013.01); *A61M 5/31536* (2013.01); *A61M 5/31541* (2013.01); *A61M 5/31553* (2013.01); *A61M 5/31563* (2013.01); *A61M 5/31593* (2013.01); *A61M 2005/3126* (2013.01); *A61M 2005/3154* (2013.01)
(58) Field of Classification Search
CPC .......... A61M 5/31541; A61M 5/31553; A61M 5/31563; A61M 5/3158; A61M 5/31593; A61M 2005/3126; A61M 2005/3154
See application file for complete search history.

(56) References Cited

U.S. PATENT DOCUMENTS

| | | | |
|---|---|---|---|
| 2012/0253287 A1* | 10/2012 | Giambattista | A61M 5/3158 604/189 |
| 2013/0041322 A1* | 2/2013 | Holmqvist | A61M 5/31525 604/189 |
| 2014/0303563 A1* | 10/2014 | Moeller | A61M 5/14566 604/189 |

* cited by examiner

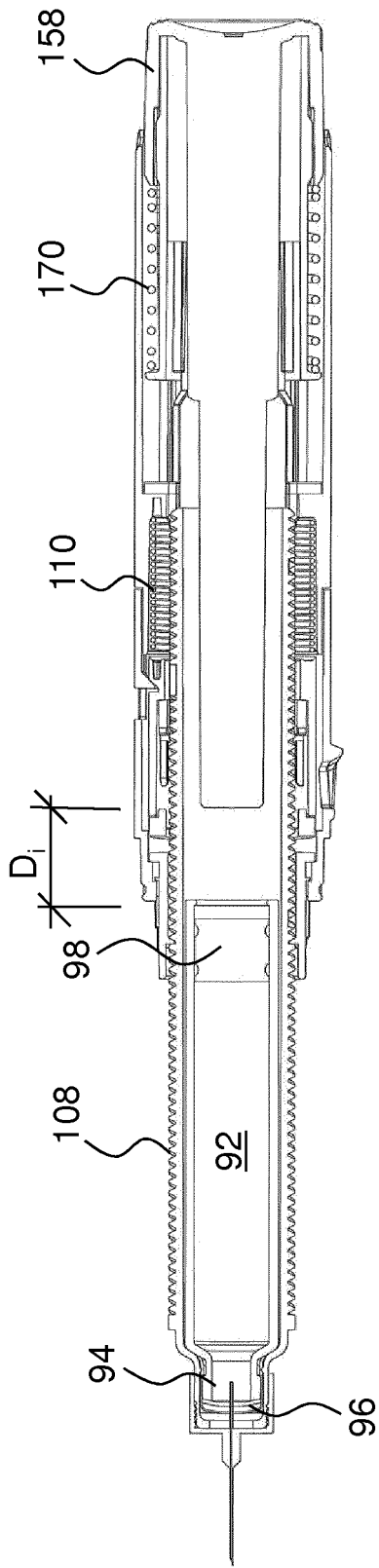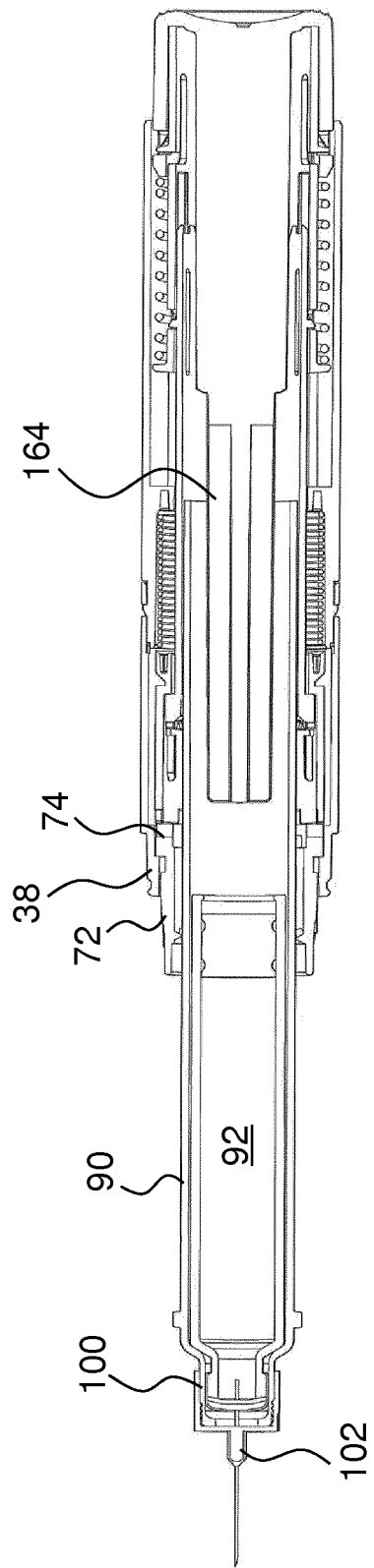

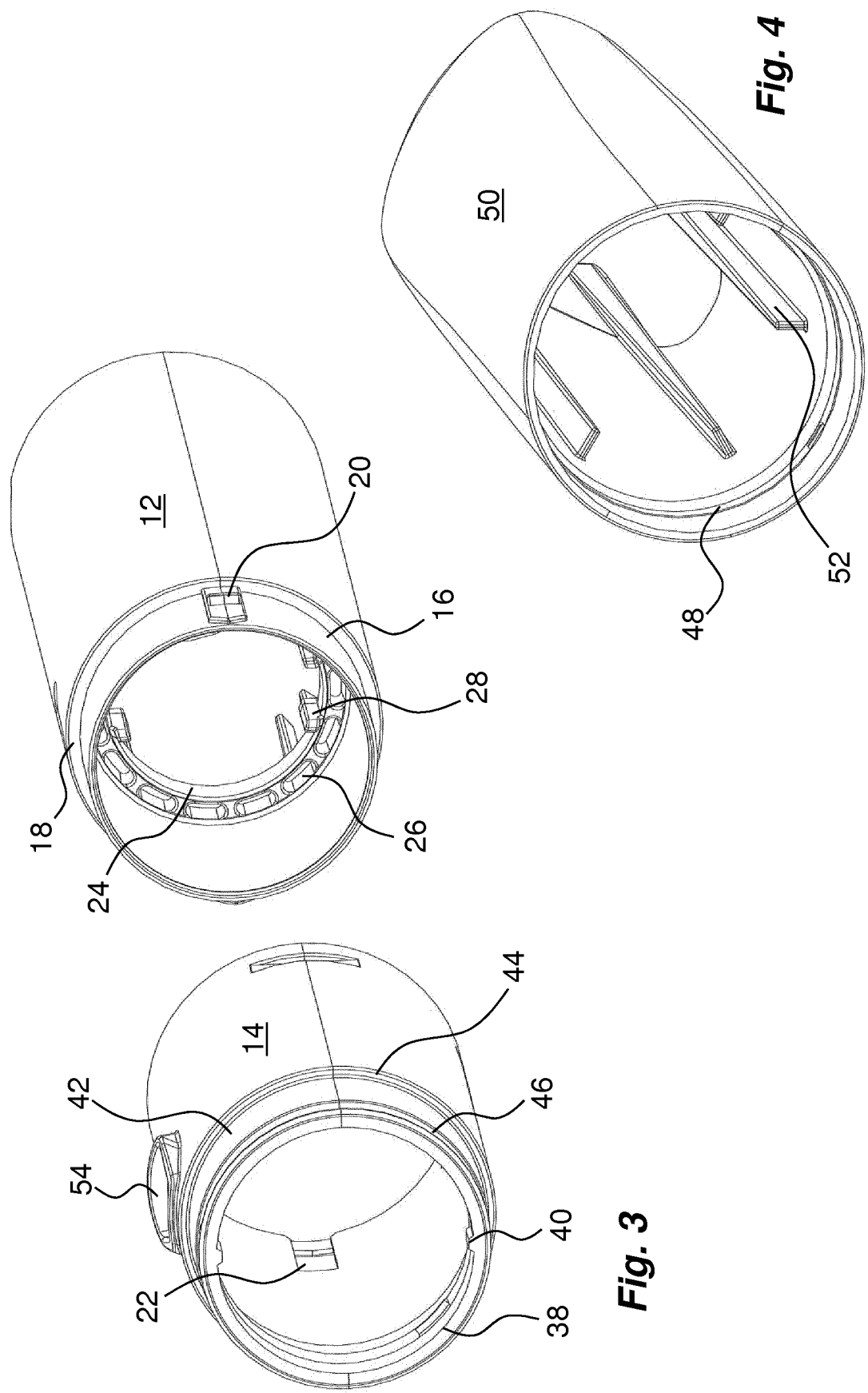

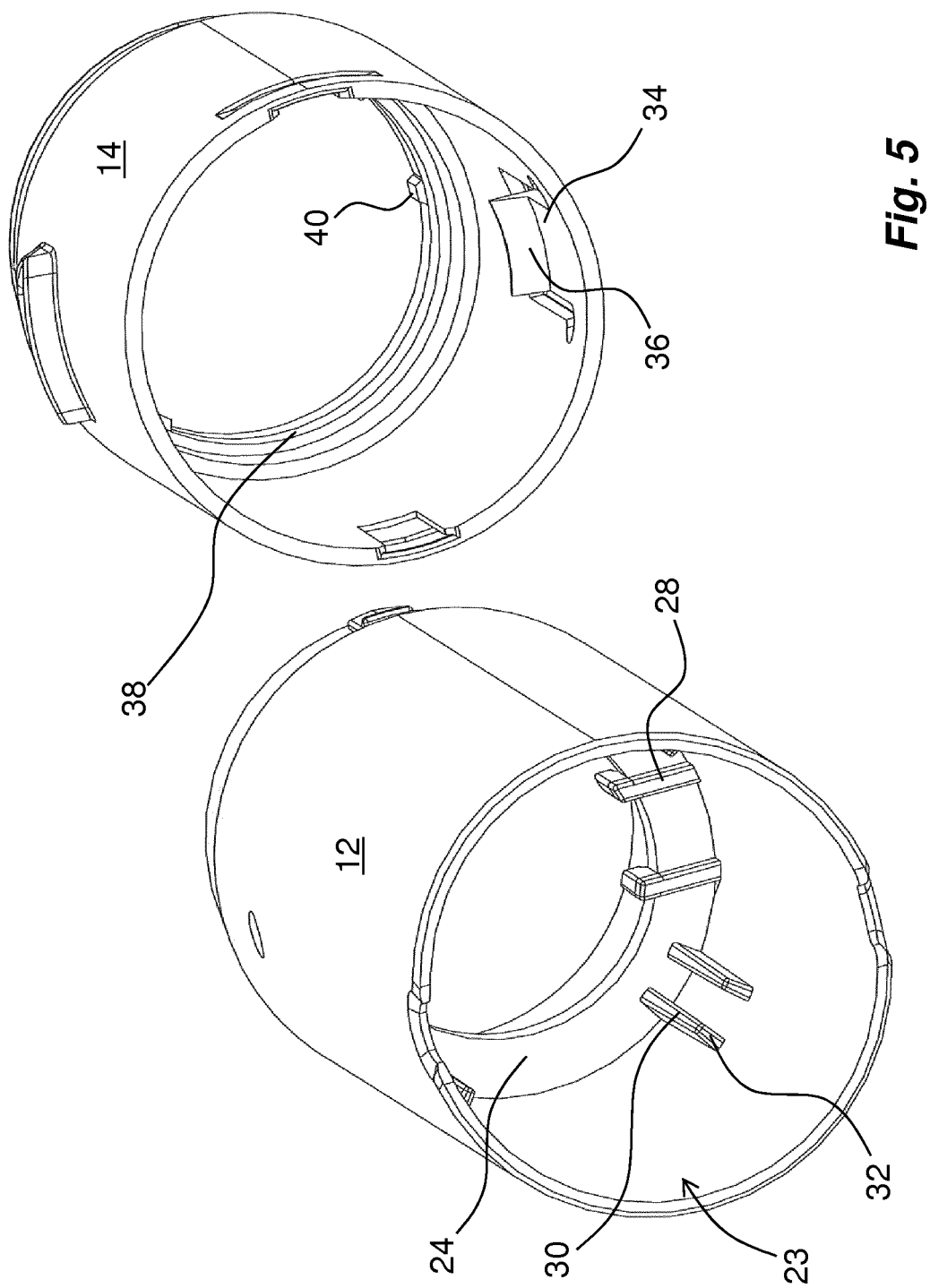

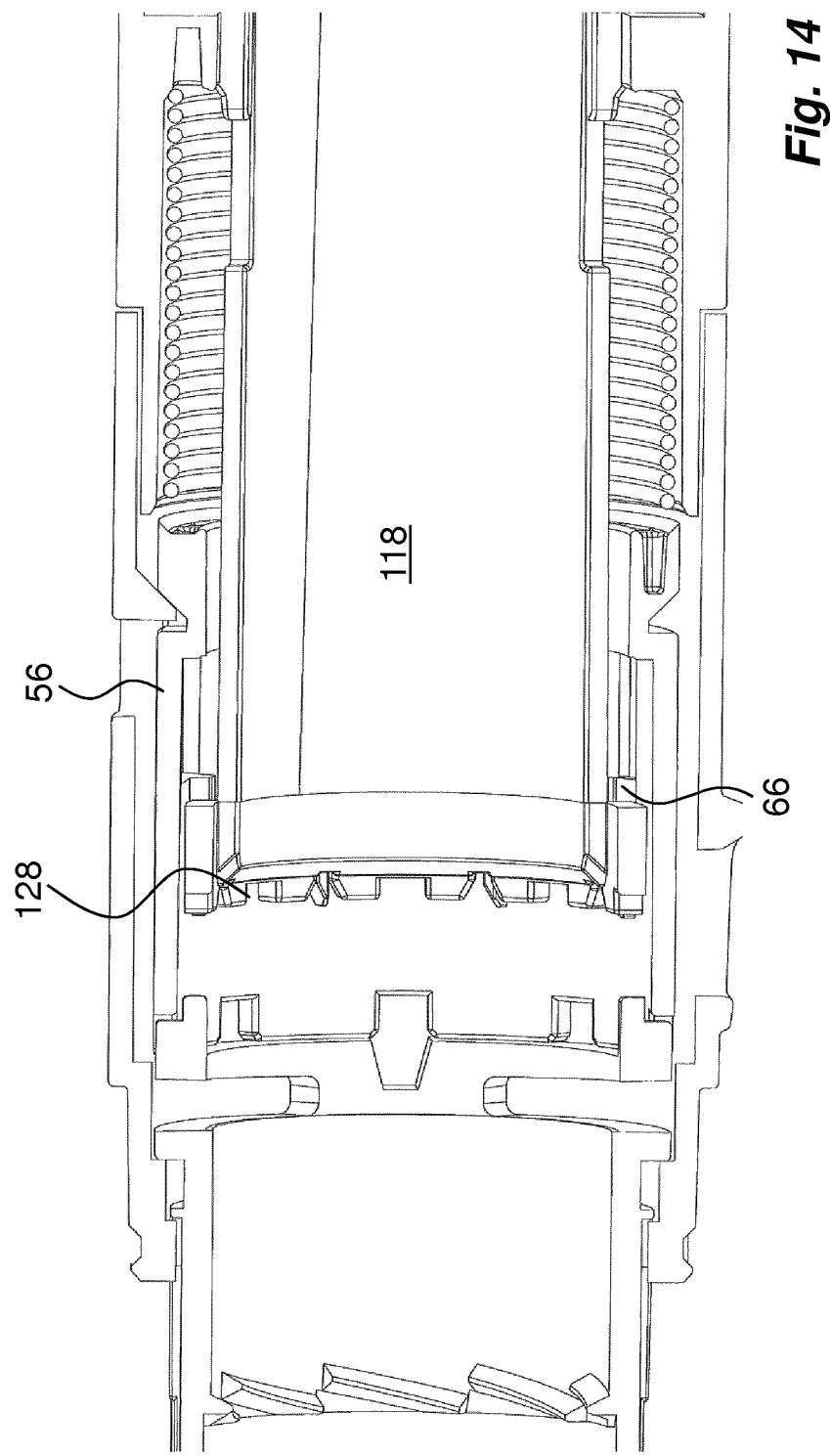

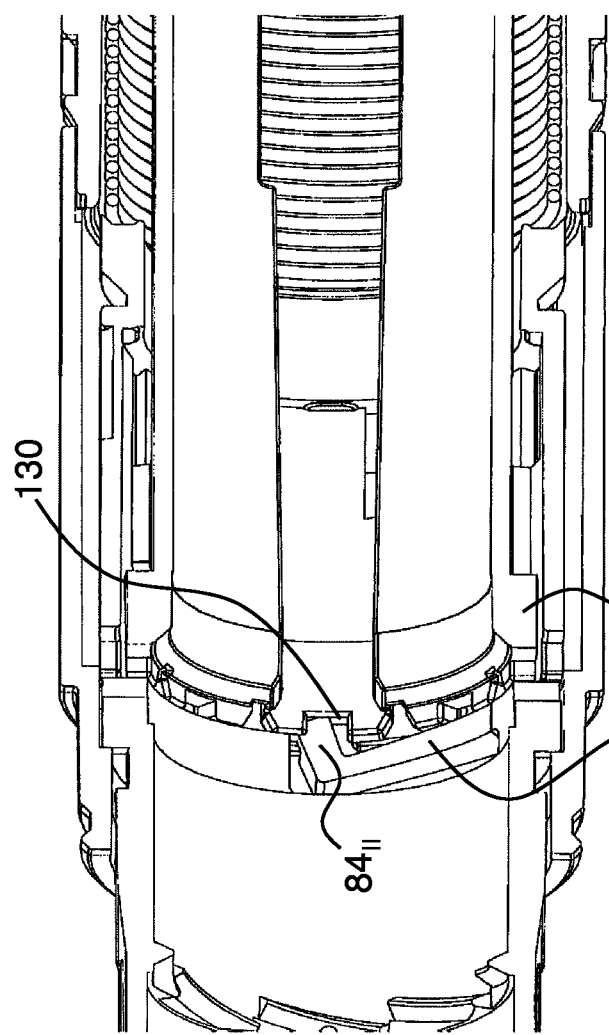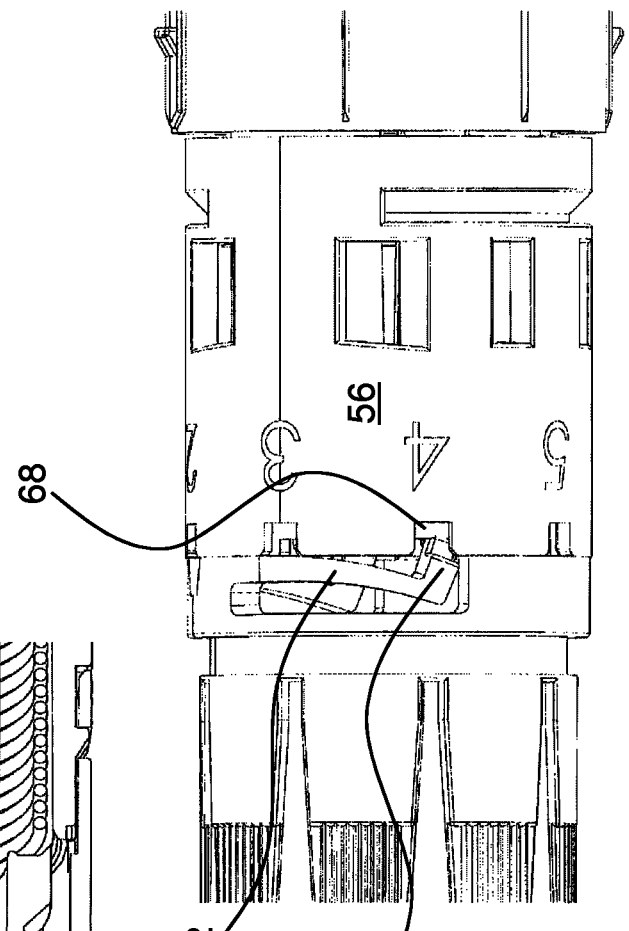

MEDICAMENT DELIVERY DEVICE

CROSS REFERENCE TO RELATED APPLICATIONS

The present application is a U.S. National Phase Application pursuant to 35 U.S.C. § 371 of International Application No. PCT/EP2016/077879 filed Nov. 16, 2016, which claims priority to Swedish Patent Application No. 1551721-2 filed Dec. 30, 2015. The entire disclosure contents of these applications are hereby incorporated by reference into the present application.

TECHNICAL AREA

The present invention relates to a medicament delivery device and in particular a medicament delivery device that is capable of having its length reduced during use of the device.

BACKGROUND OF INVENTION

Many medicament delivery devices that are out on the market for self-administering of doses of medicament are arranged with dose setting features. These may be parts of the medicament delivery device that are operable in relation to other parts, such as dose drums that are rotated in relation to a housing. In some solutions the different housing parts are moved in the longitudinal direction in relation to each other when a dose is set. For instance, the document U.S. Pat. No. 5,226,896 discloses an injection pen comprising a collar and a syringe housing in threaded engagement with each other. In order to set a dose of medicament, the syringe housing is rotated in relation to the collar, whereby the syringe housing is moved inside the collar, making the housing of the device shorter. On the other hand, when setting a dose, a distal end of the device comprising a cap attached to a distal end of a plunger rod is extended in the distal direction. This is because the proximal end of the plunger rod is in contact with a stopper in a syringe filled with medicament, and when the syringe housing is moved in the distal direction, so does the stopper, plunger rod and cap due to the incompressibility of the medicament in the syringe. Thus, the device retains more or less the same length during the setting of a dose. When then an injection is to be performed, the cap with its plunger rod is pressed linearly in the proximal direction, causing a dose delivery. Further, the pressure on the medicament in the syringe during dose setting may cause a leakage of medicament when an injection needle is attached to the proximal end of the syringe.

Document WO 2006/130098 displays a medicament delivery device comprising a proximal cartridge housing containing a cartridge. The proximal housing part is threadedly connected to a distal back cover provided with a dose indication drum. For setting a dose of medicament, the back cover is rotated in relation to the proximal cartridge housing. When the back cover is rotated, a plunger rod spring is compressed. Further, a servo spring in the form of a clock spring is also arranged to aid the plunger rod in the injection operation, and is tensioned when the back cover is rotated. In order to deliver a dose, the proximal end is pressed against an injection site, whereby the plunger rod spring and the servo spring are released by a needle shield affecting a release mechanism, which springs force the plunger rod in the proximal direction, whereby a dose of medicament is delivered.

The device according to WO 2006/130098 is rather bulky and difficult to handle and is provided with double springs which makes a somewhat complicated device in particular if the device is to be used as a disposable medicament delivery device.

Regarding device size and functional features, especially regarding disposable medicament delivery devices, there are further developments to be made.

BRIEF DESCRIPTION OF INVENTION

In the present application, when the term "distal part/end" is used, this refers to the part/end of the device, or the parts/ends of the members thereof, which during use of the device is located the furthest away from the medicament delivery site of the patient. Correspondingly, when the term "proximal part/end" is used, this refers to the part/end of the device, or the parts/ends of the members thereof, which during use of the device is located closest to the medicament delivery site of the patient.

The aim of the present invention is to remedy the drawbacks of the state of the art devices. This aim is obtained by a medicament delivery device according to the features of the independent patent claim. Preferable embodiments of the invention form the subject of the dependent patent claims.

According to one aspect of the invention, it comprises a medicament delivery device comprising a housing. The housing could be in one or several parts connectable to each other, depending on manufacturing aspects.

A medicament container holder is preferably provided to the housing, which may be movable in relation to the housing, which could be rotationally movable but preferably linearly movable in relation to the housing. The medicament container holder is designed to accommodate a medicament container, wherein the medicament container preferably is provided with a medicament delivery member for administering a dose of medicament.

The medicament delivery device is further arranged with a biased activator, wherein the biased activator comprises a plunger rod, preferably elongated, where the plunger rod is arranged to act on the medicament container for delivering a dose of medicament through the medicament delivery member when the biased activator is operated. In this respect, the biased activator may be manually operated but could of course also be driven automatically by suitable drive mechanisms comprising different types of drive springs for example.

The medicament delivery device is further arranged with a manually operable dose setting member. The dose setting member may be operably connected to both the housing and the medicament container such that manual operation of the dose setting member will cause the medicament container holder with the medicament container to move towards the plunger rod for setting a dose of medicament to be delivered. The dose setting member may be rotatably connected to the housing and may further be arranged with threads that preferably are arranged on an inner surface of a passage through the dose setting member.

The threads on the dose setting member are then arranged to cooperate with threads arranged on the medicament container holder, wherein operation of the dose setting member will cause the medicament container holder with the medicament container to move towards the plunger rod for setting a dose of medicament to be delivered. When provided with threads, the dose setting member is preferably arranged rotational in the housing such that rotation of the dose setting member causes a linear movement of the medicament container holder. It is however to be understood that the dose setting member may be provided with other types of dose setting elements such that both the dose setting member and the medicament container holder are moved linearly. Alternatively the medicament container holder may be rotated for moving the medicament container to move towards the plunger rod.

A dose drum may be releasably connected to the dose setting member. Further, a releasable connection mechanism may preferably be arranged between the dose setting member and the dose drum such that when the dose setting member is operated, the dose drum may be displaced from an initial position to a set dose position. In this position, the dose setting member and the dose drum are connected and move as one unit for setting a dose. The dose drum may be arranged with indicia in order to view a set dose. In this regard, the indicia may be numbers, a number of discrete elements such as one dot or one line for position one, two lines or dots for position two, etc.

According to a favourable solution, the medicament delivery device may further comprise a release mechanism operably connected to the biased activator. The release mechanism is operably connected to the plunger rod such that when the plunger rod is moved to an end position of the dose delivery, the release mechanism is arranged to act on the connection mechanism for releasing the dose drum from the dose setting member. Thus when the dose delivery sequence comes to an end, the dose drum is disconnected from the dose setting member and in this position the dose setting member and the dose drum are not one unit any more but can move freely in relation to each other and in particular the dose drum can move freely.

On the other hand, according to a feasible solution, the release mechanism may be provided with a locking mechanism arranged to lock the dose setting member from displacement as the connection mechanism is operated for releasing the dose drum from the dose setting member. Thus, in this position, the dose setting member is prevented from being operated by a user. This is an advantage in that the medicament container holder and thus the medicament container cannot be moved further now when the plunger rod is in contact with the stopper of the medicament container. If the dose setting were to be operated at this stage, it could move the medicament container holder and the medicament container such that additional medicament would be expelled through the medicament delivery member.

A further advantageous solution may be that the medicament delivery device further comprises a first resilient member arranged between the dose drum and the housing, which first resilient member is tensioned when a dose is set by operating the dose setting member such that the dose drum is displaced from the initial position to the set dose position, and is capable of moving the dose drum back from the set dose position to the initial position when the dose drum is released from the dose setting member. Thus, with this solution, the dose drum is automatically moved to the initial position in contrast to a manual operation by a user for resetting the dose drum.

According to one solution, the connection mechanism may comprise resiliently arranged protrusions on one of the dose setting member or dose drum engageable with cut-outs on the other of the dose drum or dose setting member. Resilient protrusions provide a releasable connection between the dose drum and the dose setting member. The resiliency may be created in many ways. Either the protrusions as such are made of a resilient material. It may also be that the protrusions are attached to or integrated with elements that display resilient properties such as arms that are bendable. Further, the resiliency may be obtained by springs.

The release mechanism may further comprise a release sleeve and the locking mechanism may comprise a number of resiliently arranged protrusions on one of the dose setting member or release sleeve engageable with a number of cut-outs on the other of the release sleeve or dose setting member. Also here the resiliency may be obtained in a number of ways. According to one solution, the protrusions may be arranged to one and the same resilient element, such as a resilient arm. Then the protrusions may protrude to different extents and/or different directions so as to cause a release of the dose drum at the same time as the dose setting member is locked. This solution provides a compact function with very few components.

According to another aspect of the invention, the release mechanism may further comprise rotational locking elements arranged to lock the dose drum and the dose setting member during delivery of the dose. This may be important so that the dose size may not be manipulated, intentionally or by accident, during the dose delivery sequence. Thus only a linear movement of the biased activator with the plunger rod as well as the release mechanism is allowed during this stage. In this respect, in order to allow rotation of the dose drum at the end of the dose delivery sequence, the rotational locking elements are arranged to release the dose drum and the dose setting member.

According to one aspect in this regard, the rotational locking elements may as an example comprise longitudinally extending grooves on one of the release mechanism and the dose drum, arranged to cooperate with longitudinally extending ribs on the other of the release mechanism and the dose drum. It is however possible to have other solutions preventing rotation, such as ribs acting on ribs, discrete protrusions sliding along ribs or ledges, just to mention a few.

According to a further aspect, the dose setting member may comprise a number of locking elements configured to interact with at least on corresponding locking element of the housing for releasably locking rotational positions of the dose setting member during setting of a dose. This has several advantages in that it provides the user with distinct dose size positions, which positions may correspond to certain indicia on the dose drum that are visible to the user during the setting of a dose. Also, when a first resilient member is used for moving the dose drum back to the initial position, when the dose setting member and the dose drum are connected as one unit during dose setting, the spring will act on both components, trying to move them back to the initial position. The dose setting member locking elements will then maintain the set position of the unit despite the force of the first resilient member.

In this regard, the dose setting member locking elements may comprise protrusions on a passage of the housing cooperating with recesses on an outer surface of the dose setting member. Further, the combination could be the other way around with protrusions on an outer surface of the dose setting member engaging recesses or grooves on a passage of the housing through which the dose setting member extends. Further, with this solution, the dose setting member locking elements will provide tactile and audible information during setting of a dose in that the protrusions will move in and out of engagement with the recesses or grooves causing sudden movement of the protrusions which will give rise to sound as well as vibrations.

Further, the medicament delivery device may comprise a dose limiting mechanism operably arranged to the dose drum and capable of limiting the maximum dose to be set so that a user cannot set a dose size that cannot be handled or delivered by the medicament delivery device. According to one possible solution, the dose limiting mechanism comprises a groove extending a distance along the circumference of the dose drum arranged to interact with a stop ledge on the housing, wherein the turning of the dose setting member will bring the stop ledges in contact with the end of the groove within one turn of the dose setting member, limiting the maximum dose to be set. It is however to be understood that other types of solutions are possible within the desired function. For instance the groove may be replaced with discrete protrusions at each desired stop position, wherein the stop ledge on the housing only comes in contact with the dose drum when it abuts one of the protrusions.

Preferably the medicament delivery device further comprises a rotational lock arranged between the medicament container holder and the housing wherein the medicament container holder can only move linearly when the dose setting member is rotated. The rotational lock may comprise at least one elongated band on the outer surface of the medicament container holder fitting into a cut-out in the housing. Further the at least one elongated band may be arranged with threads that cooperate with the threads of the dose setting member. In order to have an equal distribution of forces on the medicament container holder when the dose setting member is rotated for setting a dose, at least two elongated bands should be provided on opposite sides of the medicament container holder.

Further a last dose mechanism may be arranged, which is operably arranged to the dose setting member and capable of limiting the maximum dose to be set to the remaining quantity of medicament in the medicament container. As one feasible solution, the last dose mechanism may comprise a stop ledge in a proximal area of the medicament container holder, arranged to come in contact with, and limit the movement, of the dose setting member.

According to one feasible solution the biased activator may comprise a manually operable push button extending in a distal direction through the housing. The push button may have an end wall acting as a pushing surface for a user. On the proximal side of the end wall, the plunger rod may be attached or made integral. Since the device is intended to be used several times giving several doses of medicament before being discarded, the biased activator may comprise a return force element arranged to return the biased activator after delivery of a dose of medicament. The biased activator is then ready for a subsequent dose delivery sequence.

These and other aspects of, and advantages with, the present invention will become apparent from the following detailed description of the invention and from the accompanying drawings.

BRIEF DESCRIPTION OF DRAWINGS

In the following detailed description of the invention, reference will be made to the accompanying drawings, of which FIG. 2 is a longitudinal cross-section of the medicament delivery device of FIG. 1, FIGS. 3-12 are detailed views of components comprised in the embodiment of FIG. 1, and FIGS. 13-19 are cross-sectional views of different functional positions.

DETAILED DESCRIPTION OF THE INVENTION

Figure 1:
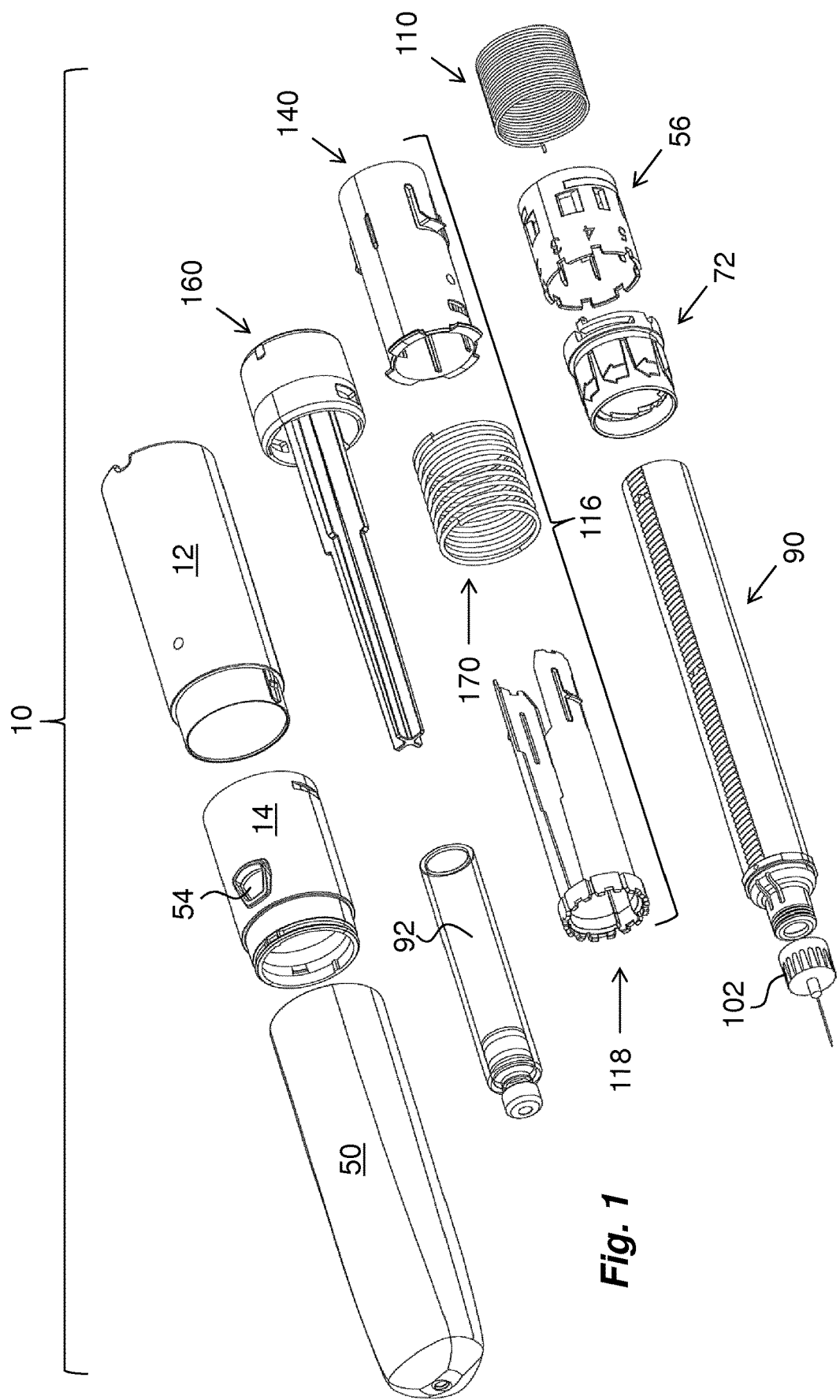
FIG. 1 is an exploded view of one embodiment of the present invention.

The embodiment of a medicament delivery device 10 shown in the drawings comprises a generally tubular housing that in the embodiment shown is in a distal housing part 12 and proximal housing part 14. The distal housing part 12 is arranged with a first proximal area 16, FIG. 3, having a diameter somewhat smaller than the rest of the housing part, creating a proximally directed circumferential ledge 18. The first proximal area 16 is further arranged with a number of outwardly directed protrusions 20. These protrusions 20 are arranged to be snap-fitted into recesses 22 in a distal area of the proximal housing part 14, such that the two housing parts are connected to each other with a distal part of the proximal housing part 14 covering the proximal area 16 and with a distal end surface in contact with the proximally directed ledge 18.

The distal housing part 12 is provided with a distally directed passage 23, FIG. 5, and is further arranged with an annular ledge 24, which ledge 24 is provided with a number of recesses 26, FIG. 3, on its proximally directed surface. The annular ledge 24 is further arranged with radially inwardly directed guide ledges 28, FIG. 5, the function of which will be described below. Further, a number of longitudinally directed ledges 30 are arranged on the inner surface of the distal housing part 12, which ledges 30 have distally directed end surfaces 32.

The proximal housing part 14 is provided with a proximally directed tongue 34 formed by a U-shaped slit in the housing wall, FIG. 5. The free end of the tongue 34 is arranged with an inwardly directed ledge 36. At the proximal end of the proximal housing part an annular inwardly directed ledge 38 is arranged. The annular ledge 38 is provided with a number of inwardly directed protrusions 40 configured to interact with a dose setting member as will be explained. The proximal end of the proximal housing part 14 is further arranged with an area 42, FIG. 3, with somewhat reduced diameter than the rest of the proximal housing part, creating a proximally directed ledge 44. The area 42 is further arranged with a groove 46 extending around the circumference of the proximal housing part 14. The groove 46 is intended to accommodate an annular protrusion 48 that is placed on an inner surface of a protective cap 50, FIG. 4. The protective cap 50 is designed to fit onto the proximal area 42 of the proximal housing part, wherein a distal end surface of the protective cap 50 is abutting the ledge 44. In this position, the annular protrusion 48 fits into the groove 46, providing a releasable grip between the protective cap 50 and the proximal housing part 14. The inner surface of the protective cap 50 is arranged with support and guide ridges 52. The proximal housing part is further arranged with an opening or window 54, FIGS. 1 and 3.

Figure 6:
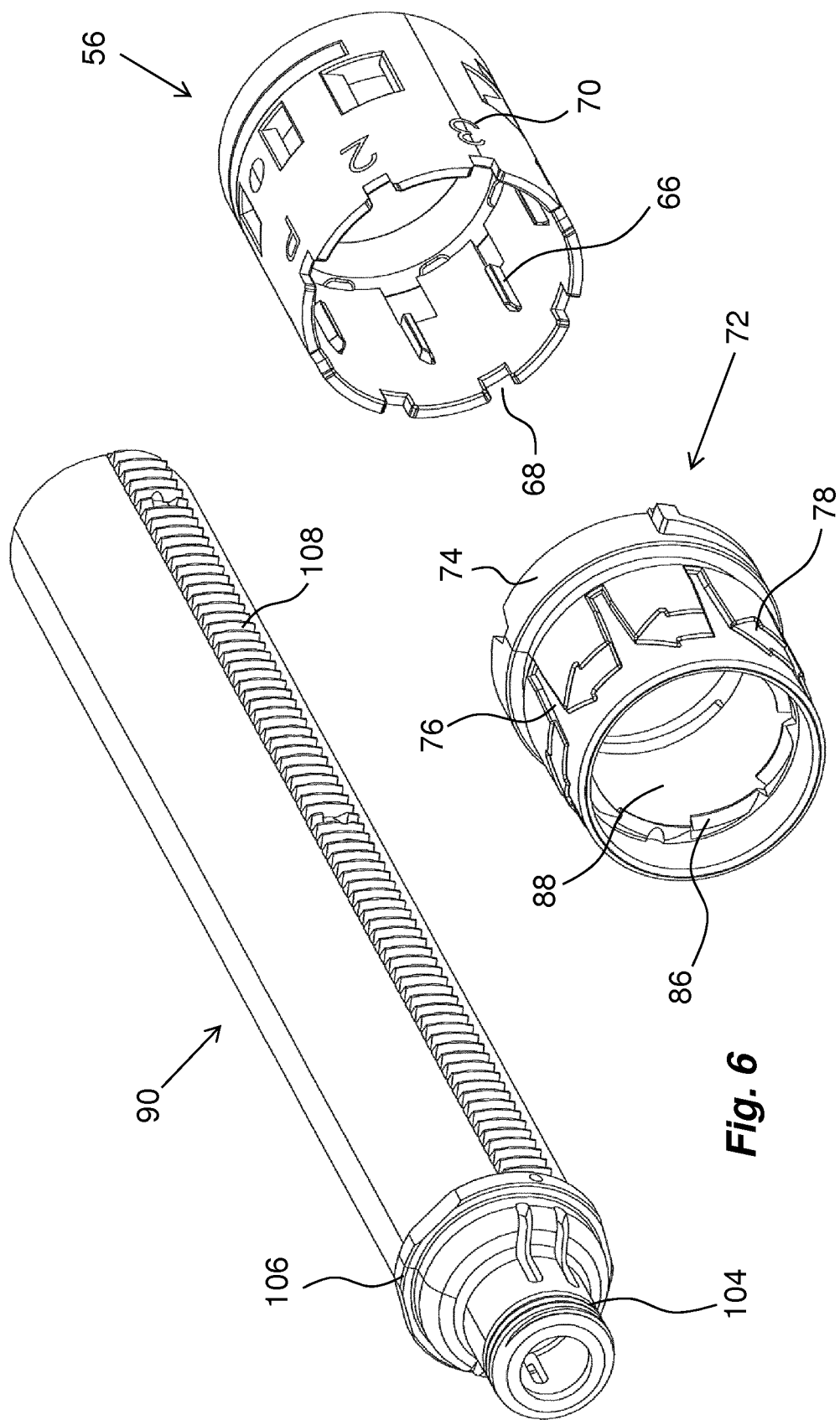
Figure 7:
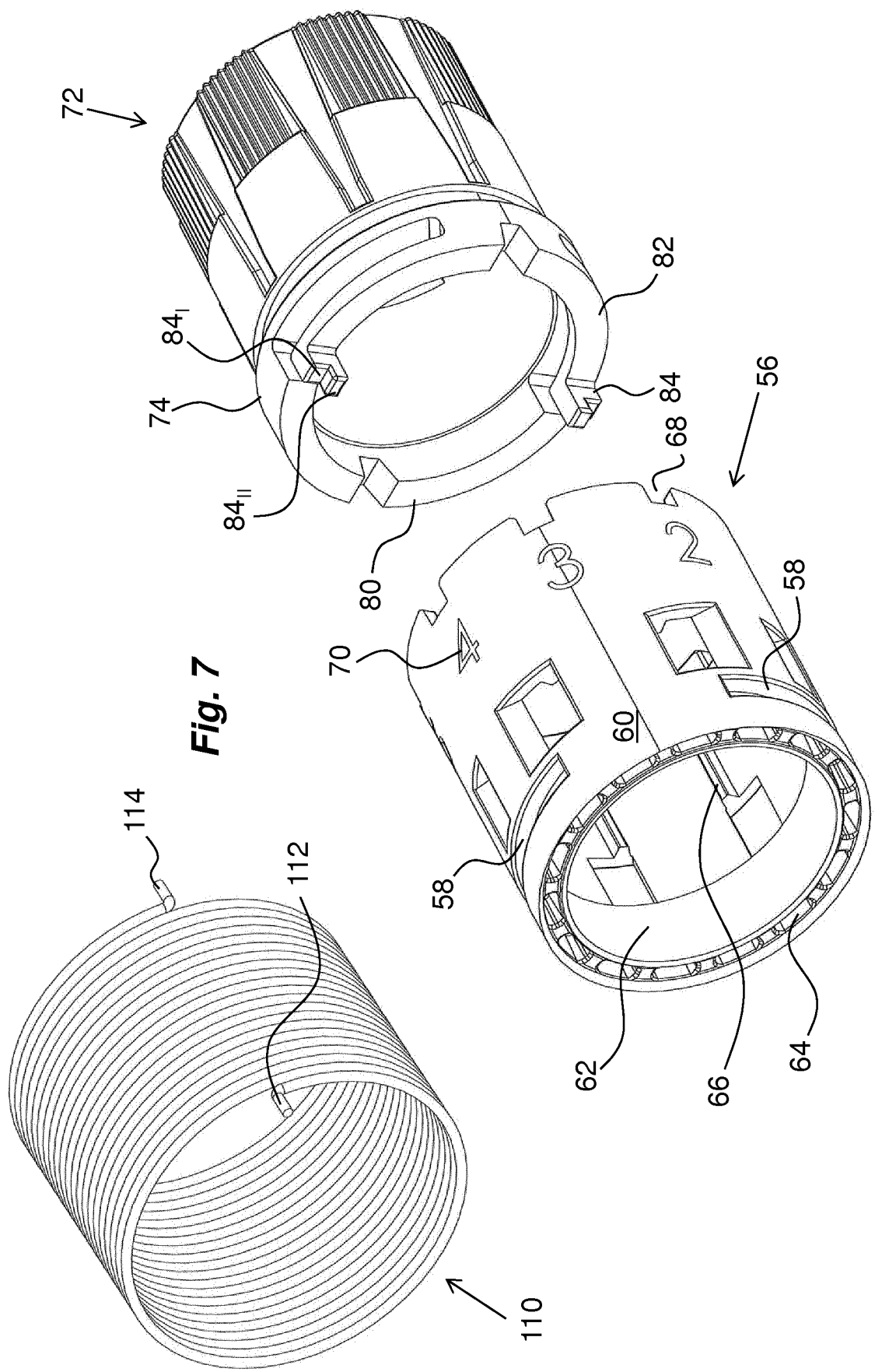

The medicament delivery device 10 is further provided with a generally tubular dose drum 56, FIGS. 6 and 7. The outer diameter of the dose drum 56 is somewhat smaller than the inner diameter of the proximal housing part 14 so that the dose drum 56 may be placed inside and coaxial with the proximal housing part 14. The outer surface of the dose drum 56 is arranged with a groove 58, FIG. 7, extending in a circumferential direction on the outer surface of the dose drum 56. The groove 58 does not extend the full circumference but is interrupted by a bridging area 60. The ledge 36 of the tongue 34 of the proximal housing part 14 is intended to fit into the groove 58 of the dose drum 56. The ledge 36 and the groove 58 enables turning of the dose drum 56 in relation to the proximal housing part 14 almost a full turn, stopped by the bridging area 60, and preventing axial relative movement.

The distal area of the dose drum 56 is arranged with an annular ledge 62, wherein a distally directed surface of the ledge 62 is provided with a number of recesses 64. On the inner surface of the dose drum 56, a number of longitudinally extending ribs 66 are arranged. Further, the dose drum 56 has a proximally directed end surface, which end surface is arranged with generally rectangular cut-outs 68 around its circumference, comprised in a connection mechanism. Also, the outer surface of the dose drum 56 is arranged with indicia 70 such as numbers, which indicia 70 are shown in the opening or window 54 in the proximal housing part 14.

Adjacent the dose drum 56 a generally tubular dose setting member 72 is arranged, FIGS. 6 and 7. The dose setting member 72 is provided with an annular ledge 74 at its distal end and the diameter of the dose setting member 72 is chosen somewhat smaller than the inner diameter of the proximal housing part 14. A proximal surface of the annular ledge 74 of the dose setting member 72 is intended to be in contact with a distally directed surface of the annular ledge 38 of the proximal housing part as seen in FIG. 2b, limiting the movement in the longitudinal proximal direction of the dose setting member 72 in relation to the proximal housing part 14. Further the ledges 38, 74 are positioned such that a major part of the dose setting member 72 protrudes out of the proximal end of the proximal housing part 14 as seen in FIG. 2.

The outer surface of the dose setting member 72 that is extending through the proximal housing part 14 is preferably arranged with grip elements such as grooves 76 providing a grip surface, and also form part of a dose setting member locking element. The grooves 76 are intended to cooperate with the inwardly directed protrusions 40 on the annular ledge 38 of the proximal housing part 14 so as to provide distinct positions between the dose setting member 72 and the proximal housing part 14 as well as tactile and audible information to a user as will be described. The grip surface of the dose setting member 72 may also be arranged with indicia such as arrows 78, providing information to a user which direction the dose setting member 72 should be rotated, as will be described below.

The dose setting member 72 is further arranged with a distally directed circumferential end surface 80, FIG. 7. On the end surface 80, two generally circumferentially extending arms 82 are arranged, which arms 82 are flexible in the longitudinal direction of the medicament delivery device. The free ends of the arms 82 are provided with distally directed protrusions 84. As seen in FIG. 7, the protrusions are designed with two sections, an outer section $84_I$ and an inner section $84_{II}$ as seen in a radial direction, wherein the inner section $84_{II}$ extends further in the distal direction than the outer section $84_I$ as will be explained. The outer section $84_I$ is arranged to fit into the rectangular cut-outs 68 of the dose drum 56, being a part of the connection mechanism. The dose setting member 72 is provided with thread segments 86 in a central passage 88 in the dose setting member 72, FIG. 6.

The medicament delivery device 10 is further arranged with a generally tubular, elongated, medicament container holder 90, FIGS. 1 and 6, which is arranged to fit into the housing parts via the central passage 88 in dose setting member 72. The medicament container holder 90 is designed to accommodate a medicament container 92, which medicament container is arranged with a neck portion 94 arranged with a penetrable septum 96 and stopper 98 movable inside the medicament container 92, FIG. 2a. When fitted into the medicament container holder 90, its neck portion 94 fits into a proximal neck portion 100 of the medicament container holder 90 as seen in FIG. 2b. The neck portion 100 of the medicament container holder 90 is arranged with attachment elements 104 for releasably attaching a medicament delivery member 102, in the embodiment shown an injection needle. The attachment elements 104 may be threads as shown, but may instead be of other types, such as bayonet fittings, luer connection etc. An annular shoulder 106 is further arranged on an outer surface of the medicament container holder 90 at a proximal area thereof.

The medicament container holder 90 is arranged with two elevated bands of thread segments 108 on its outer surface, on opposite sides thereof. The thread segments 108 are arranged to cooperate with the thread segments 86 of the dose setting member 72 as will be described. Further the bands of thread segments 108 are designed to fit between the inwardly directed guide ledges 28 of the distal housing part 12, thereby providing support and guidance of the medicament container holder 90 in the longitudinal direction as well as preventing rotation of the medicament container holder 90 in relation to the housing parts.

Figure 8:
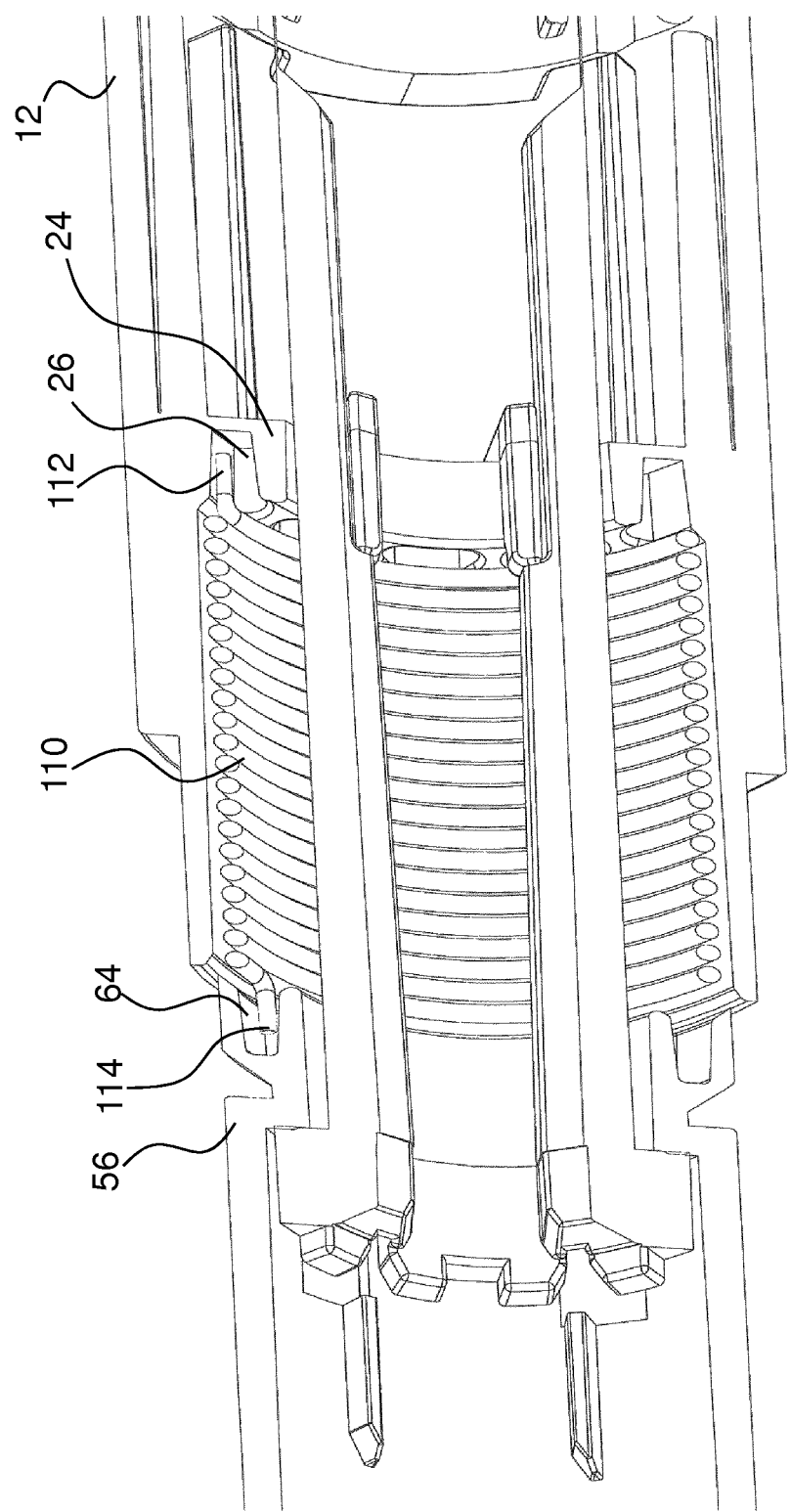

A first resilient member 110, FIG. 7, which is a torsion spring in the presented embodiment, is arranged coaxial with the distal housing part 12 and having a distal end 112 of the drum spring 110 seated in the recesses 26 of the annular ledge 24 of the distal housing part 12 and a proximal end 114 of the first resilient member 110 seated in the recesses 64 of the dose drum 56 as seen in FIG. 8.

Figure 9:
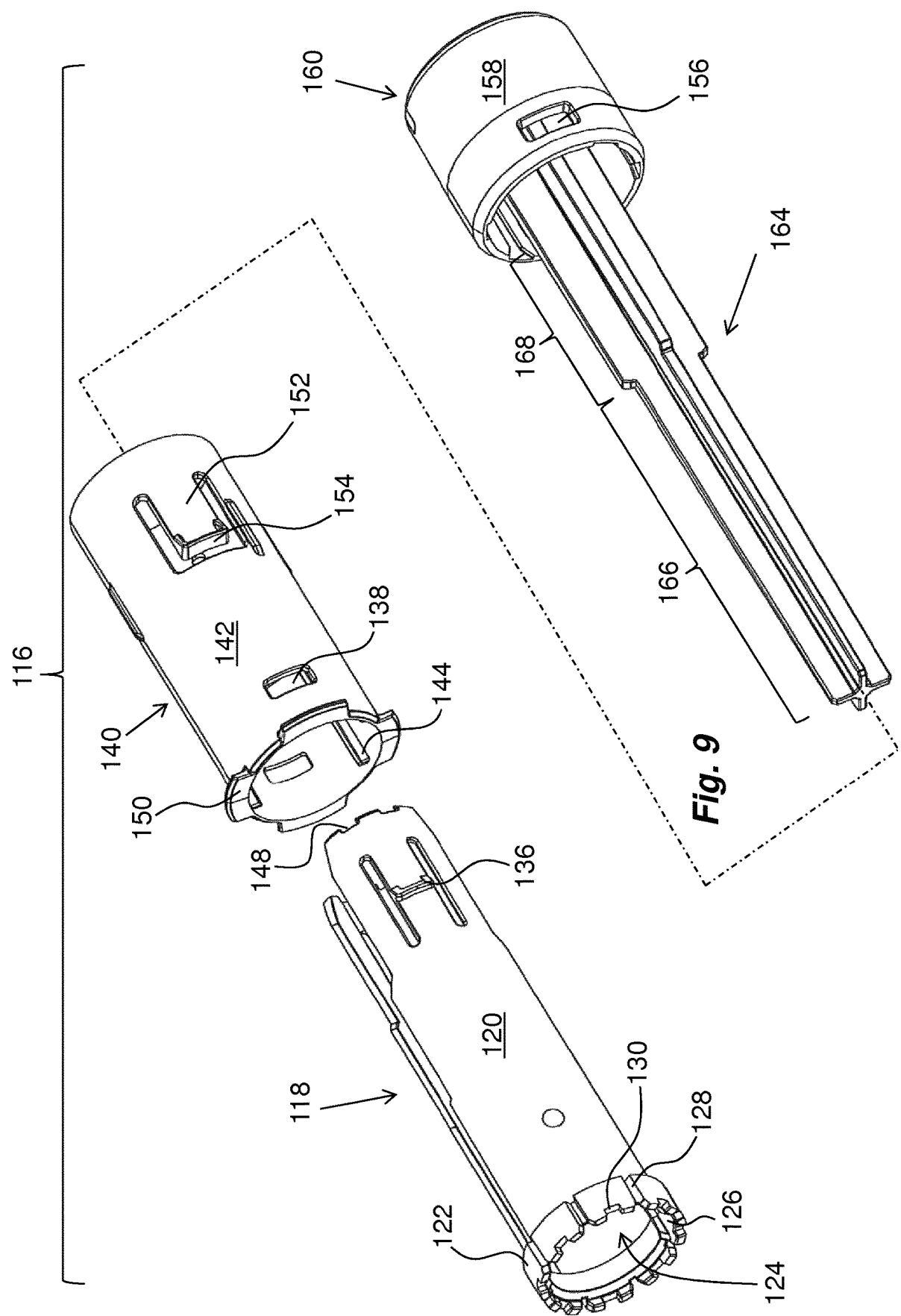

Further, a release mechanism 116, FIGS. 1 and 9, is arranged in the medicament delivery device 10. It comprises a release sleeve 118, FIGS. 9 and 10, having a generally tubular body 120, which body 120 is provided with an annular ledge 122 that has a diameter somewhat smaller than the inner diameter of the dose drum 56. The release sleeve 118 and the dose drum 56 are arranged such that a proximally directed surface of the ledge 62 of the dose drum 56 is in contact with a distally directed surface of the annular ledge 122 of the release sleeve 118. The release sleeve 118 has a passage 124 with a diameter somewhat larger than the diameter of the medicament container holder 90, where the latter extends into the passage 124. The passage 124 is further arranged with cut-outs 126 in which the bands of thread segments 108 of the medicament container holder 90 fit, creating a rotational lock between the medicament container holder 90 and the release mechanism 116.

Figure 10:
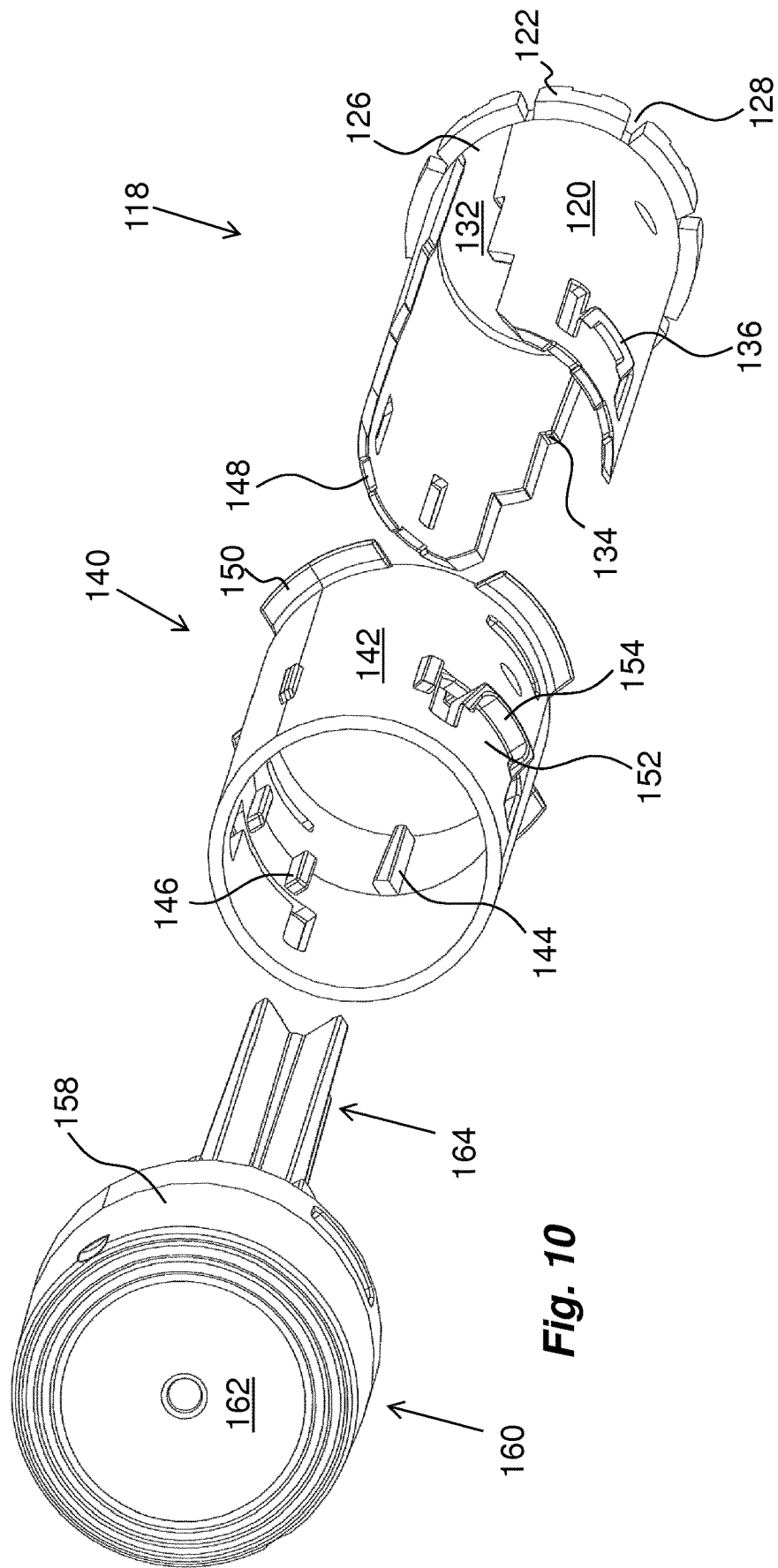

The annular ledge 122 of the release sleeve 118 is arranged with a number of longitudinally extending grooves 128 on its outer surface, which grooves 128 are to interact with the ribs 66 of the dose drum 56 as will be described. The proximally directed edge of the annular ledge 122 of the release sleeve 118 is further arranged with generally rectangular cut-outs 130, which cut-outs 130 are designed to interact with the inner sections $84_{II}$ of the protrusions 84 of the arms 82 of the dose setting member 72 as will be described. The body 120 of the release sleeve 118 is arranged with two oppositely positioned longitudinally extending slots 132. Each slot is provided with distally directed ledges 134 as seen in FIG. 10.

Figure 11:
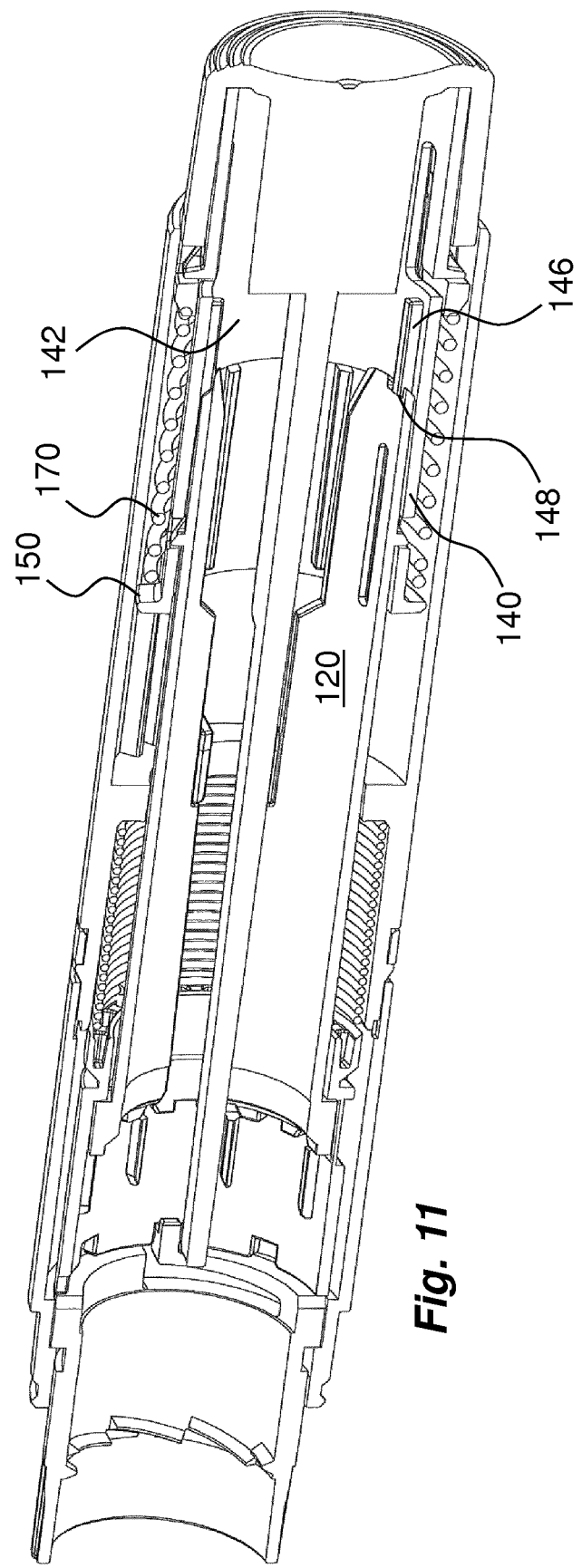

At the distal end of the release sleeve 118 two wedge-shaped outwardly extending protrusions 136 are arranged on opposite sides. These protrusions 136 are intended to fit into recesses 138 in a lock sleeve 140, FIGS. 9 and 10, which lock sleeve 140 has a generally tubular body 142. The inner surface of the body 142 of the lock sleeve 140 is arranged with longitudinally extending ribs 144 that act as support surfaces for the release sleeve 118 in that they are in contact with side surfaces of the slots 132. Further support ribs 146 are arranged on the inner surface of the body 142 of the lock sleeve 140, which support ribs 146 have proximally directed end surfaces that are intended to fit into cut-outs 148 on distally directed end surfaces of the release sleeve 118, thereby providing a stop in the distal direction of the release sleeve 118 in relation to the lock sleeve 140 as seen in FIG. 11.

The lock sleeve 140 is further arranged with a number of outwardly directed ledges 150 at the proximal end of the lock sleeve 140, the function of which will be described below. At the distal end of the lock sleeve 140 proximally directed arms 152 are provided, created by generally U-shaped cut-outs in the body 142 of the lock sleeve 140. The free ends of the arms 152 are provided with outwardly directed, wedge-shaped, protrusions 154. These protrusions 154 are intended to fit into recesses 156 in a generally tubular body 158 of a biased activator 160, FIGS. 9 and 10. The tubular body 158 is arranged with an end wall 162, FIG. 10, and extends through the distally directed passage 23 in the distal housing part 12, FIG. 2a.

The distal part of the biased activator 160 will function as a manually operable activation button as will be described. A plunger rod 164 is attached to, or made integral with, a proximally directed surface of the end wall 162. In the embodiment shown, the plunger rod 164 has a general cross-shape as seen in a cross-section. The plunger rod 164 is extending in the proximal direction towards the medicament container 92 as can be seen in FIG. 2a. The plunger rod 164 has a first proximal section 166 with cross-sectional measurements that are somewhat smaller than the inner diameter of the medicament container 92. The plunger rod 164 is also arranged with a second distal section 168 having cross-sectional measurements that are somewhat smaller than the inner diameter of the medicament container holder 90, providing lateral support for the plunger rod 164 as it advances during a dose delivery sequence.

Figure 12:
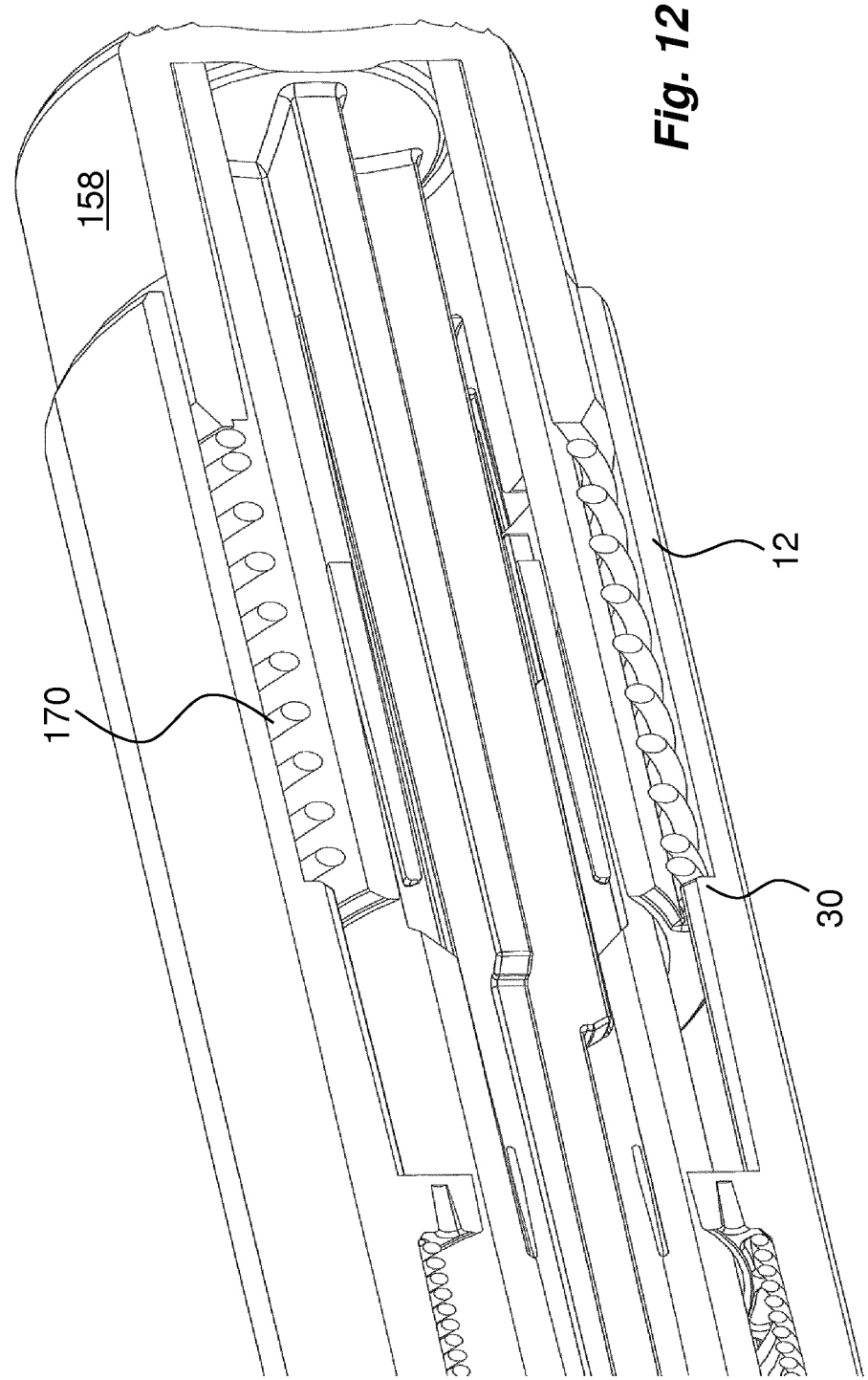

A second resilient member 170, FIGS. 1 and 12, which is a compression spring in the present embodiment, is arranged between a proximally directed end surface of the body 158 of the biased activator 160 and the distally directed end surfaces 32 of the ledges 30 of the distal housing part 12. The proximal end of the second resilient member 170 further rests against distally directed surfaces of the ledges 150 of the lock sleeve 140, FIG. 11.

The device is intended to function as follows. When the user is to administer a dose of medicament, the protective cap 50 is removed. For setting a dose the dose setting member 72 is rotated in relation to the housing 12, 14. Because of the threaded connection between the dose setting member 72 and the medicament container holder 90 by the thread segments 86 of the dose setting member 72 engaging the threaded bands 108 of the medicament container holder 90, the medicament container holder 90 will move, together with the medicament container 92, in the distal direction. The outer sections $84_I$ of the protrusions 84 of the arms 82 of the dose setting member 72 are in engagement with the cut-outs 68 of the dose drum 56, whereby the dose drum 56 will also rotate. The indicia 70 on the dose drum 56 will be displayed through the window 54, indicating the set dose.

As the dose drum 56 rotates, the first resilient member 110 will be tensioned because the proximal end 114 of the first resilient member 110 is in engagement with the recesses 64 of the dose drum 56 and the distal end 112 of the first resilient member 110 is in engagement with the recesses 26 of the stationary ledge 24 of the distal housing part 12. During the setting of the dose by turning the dose setting member 72, the inwardly directed protrusions 40 on the proximal housing part 14 will move in and out of the recesses 76 due to the flexing properties of the material of the dose setting member 72 as well as of the proximal housing part 14, causing an audible and tactile response. The protrusions 40 placed in the recesses 76 will also hold the dose setting member 72 and thus the dose drum 56 in a set position against the force of the first resilient member 110.

The maximum dose to be set is limited by the groove 58 of the dose drum 56 and the inwardly directed ledge 36 of the proximal housing part 14 in that the inwardly directed ledge 36 will come in contact with the with the end of the groove 58 when the dose drum 56 has been rotated a certain distance, which is less than a full turn. However, within this rotational range, it is possible to turn up and down the dose size as desired by the user.

Figure 13A:
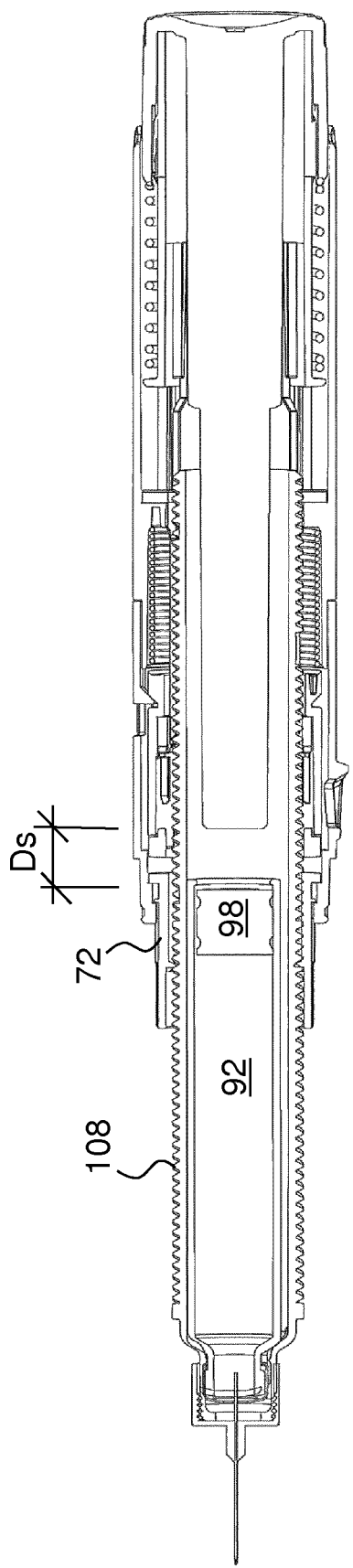
Figure 13B:
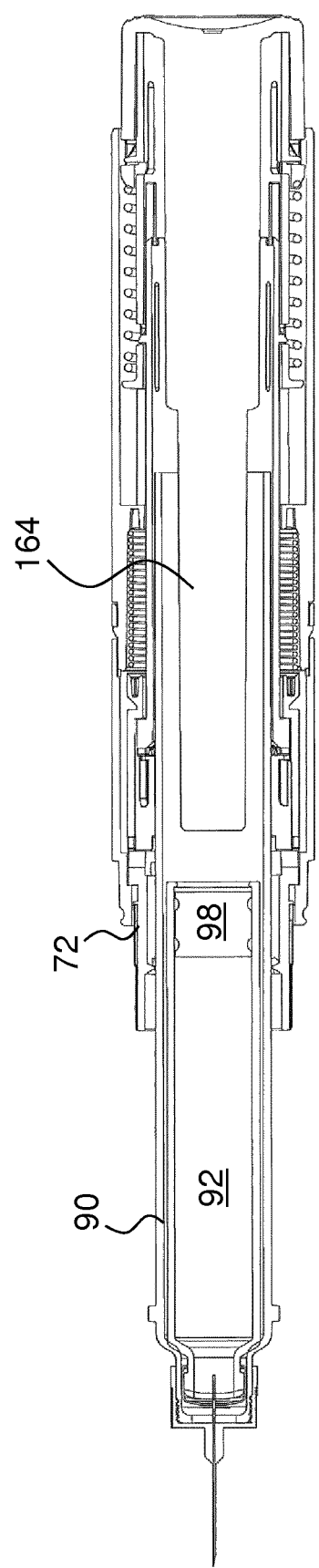

It is further to be noted that the plunger rod 164 is designed and positioned such in an unaffected initial position that its proximal end does not come in contact with the stopper 98 of the medicament container 92 even when a a maximum dose has been set, in which position the medicament container holder 90 and the medicament container 92 have been moved a maximum distance in the distal direction. FIG. 13 shows a set dose when the medicament container holder 90 and the medicament container 92 have moved distally from an initial position with a distance $D_i$ between the distal end surface of the stopper and the proximal end of the plunger rod as seen in FIG. 2a to a set position with a distance $D_s$ as seen in FIG. 13.

When the dose has been set, a medicament delivery member 102 is attached to the proximal end of the medicament container holder 90. In the embodiment shown the medicament delivery member 102 is an injection needle that is screwed onto the neck portion 100 of the medicament container holder 90. The injection needle is then arranged with a distally directed pointed end that will penetrate the septum 96 of the medicament container 92. The user then places the medicament delivery device at the dose delivery site, causing a penetration of the injection needle. The activation tubular body 158 of the biased activator 160 is then pressed in the proximal direction. First, the plunger rod 164 will be moved proximally the distance $D_s$ without being in contact with the stopper 98 of the medicament container 92, FIG. 13, where the distance is dependent on the set dose, wherein a larger dose will provide a shorter distance and a smaller dose a larger distance.

During the movement of the biased activator 160 in the proximal direction the lock sleeve 140 is also moved in the proximal direction due to the connection with biased activator 160. Also the release sleeve 118 will move in the proximal direction due to the connection with the lock sleeve 140. The movement of the release sleeve in the proximal direction will cause the grooves 128 to be moved in engagement with the longitudinal ribs 66 on the inner surface of the dose drum 56, thereby locking the dose drum 56 from rotation, FIG. 14.

Figure 15A:
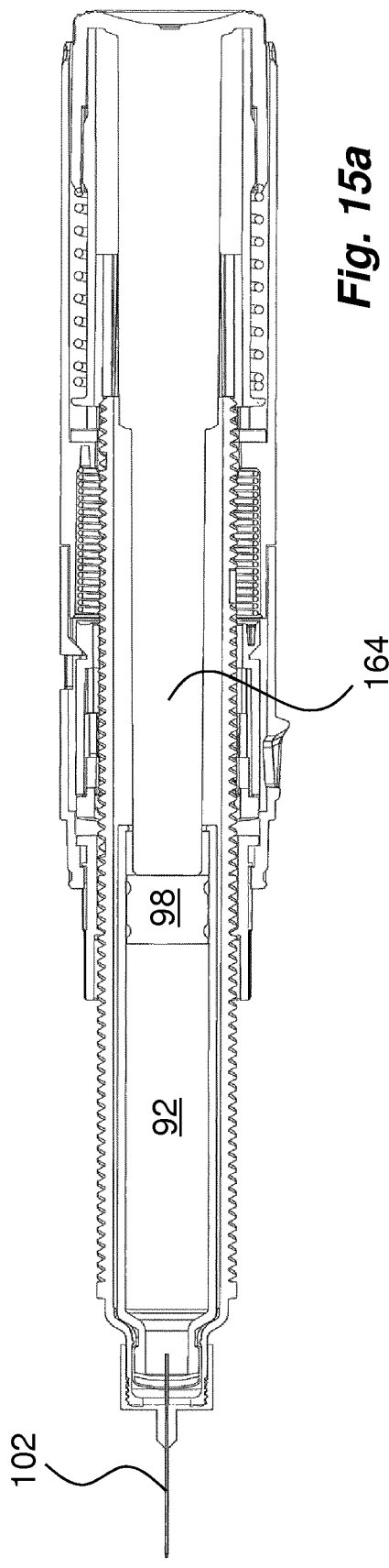
Figure 15B:
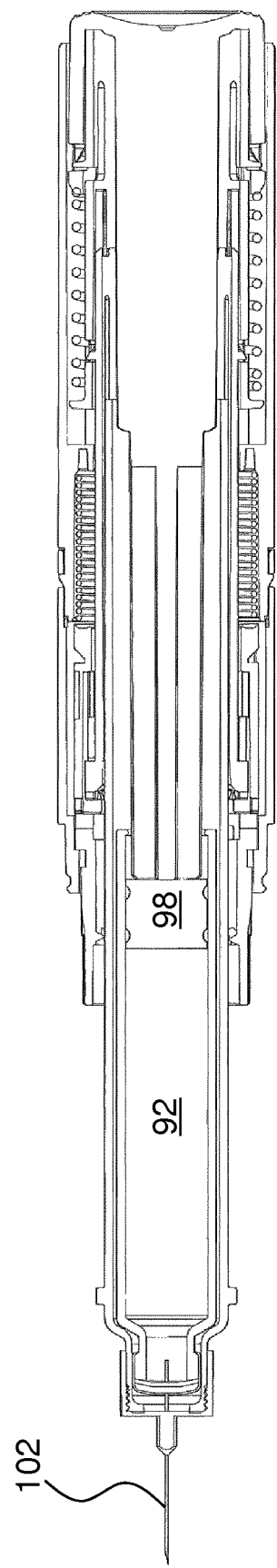
Figure 16:
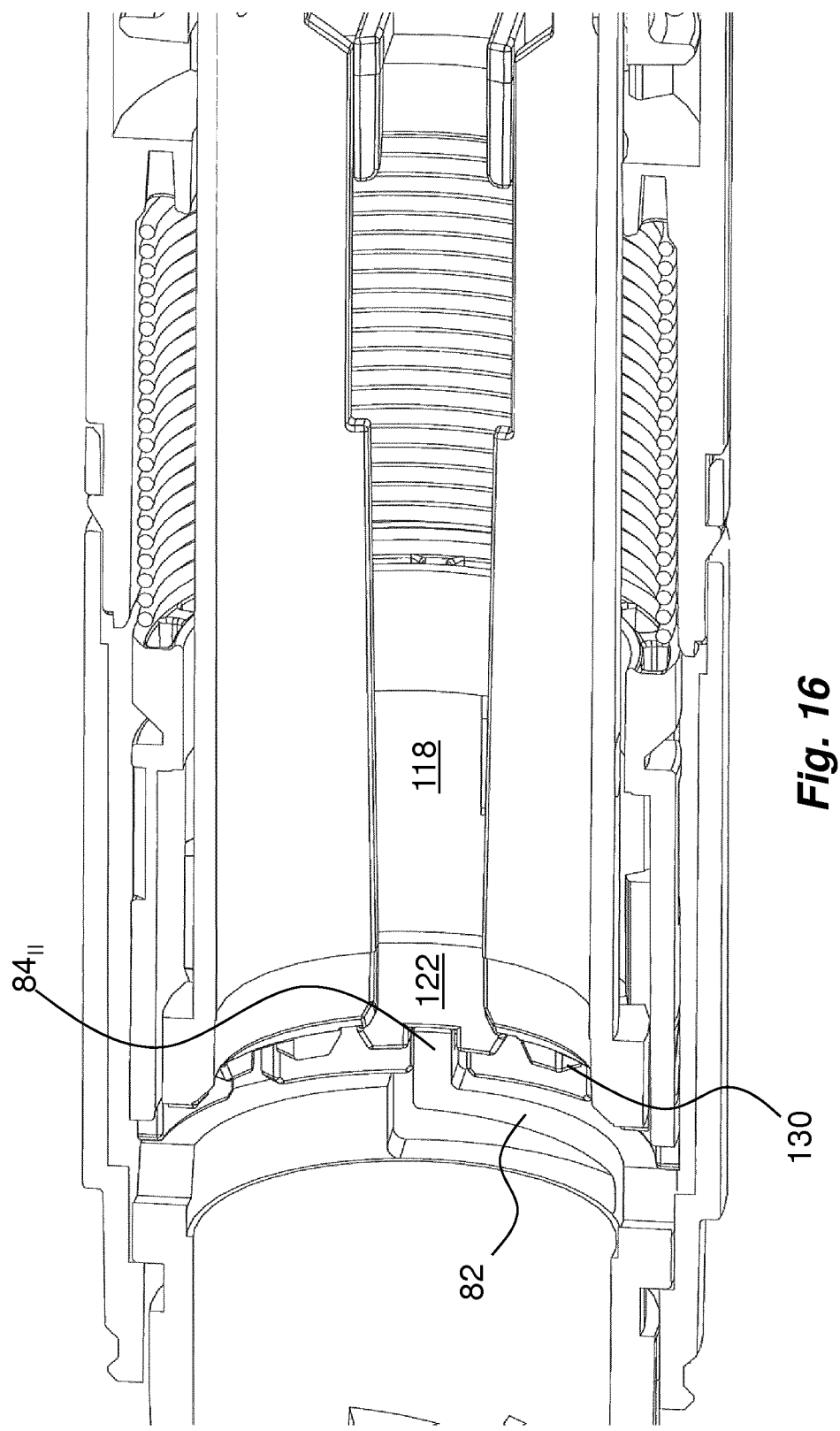

When the plunger rod 164 has moved this distance, it comes in contact with the stopper 98 and pushes it in the proximal direction, causing delivery of the set dose of medicament through the medicament delivery member 102, FIG. 15. The movement of the biased activator 160 in the proximal direction will now cause the annular ledge 122 of the release sleeve 118 to come in contact the distal end of the dose setting member 72, whereby the inner sections $84_{II}$ of the protrusions 84 of the arms 82 will fit into the rectangular cut-outs 130 of the annular ledge 122, FIG. 16, wherein the arms 82 will bend in the longitudinal direction as seen in FIG. 17, and the dose setting member 72 will be rotationally locked so that a user cannot manipulate or set a dose at this stage. The dose delivery sequence has now ended.

Figure 19:
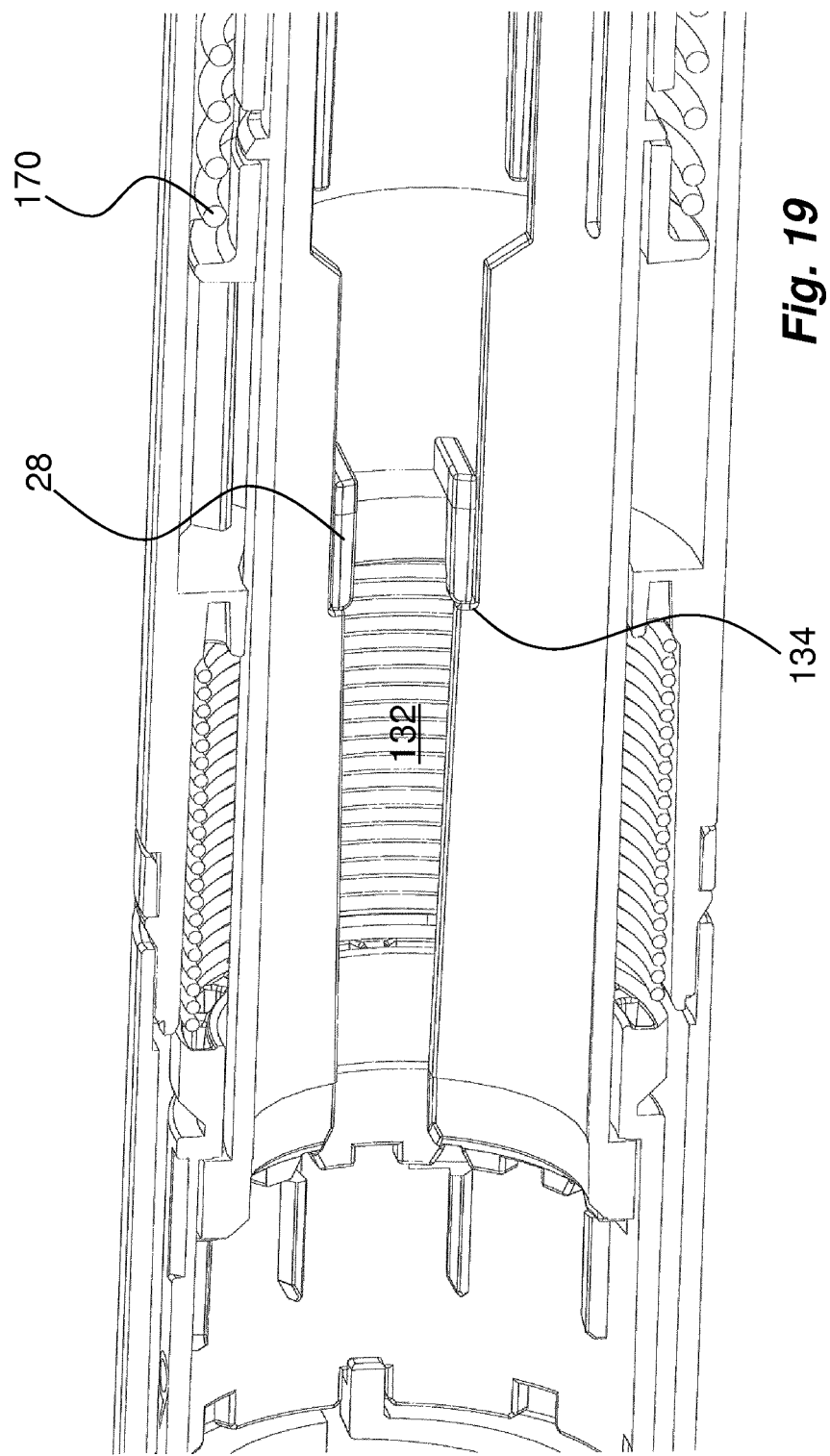

The bending of the arms 82 will in turn cause the outer sections $84_I$ to be moved out of engagement with the cut-outs 68 of the dose drum 56, FIG. 18. Also the grooves 128 on the annular ledge 122 have moved out of contact with the longitudinal ribs 66 of the dose drum 56 in this position, whereby the dose drum 56 is free to rotate and the release of the dose drum 56 will cause it to rotate back to its initial position by the force of the first resilient member 110. The stop of the biased activator 160 and the return of the dose drum 56 will inform the user that it is safe to remove the medicament delivery device 10 from the dose delivery site. The user then releases the biased activator 160, whereby it is moved distally back to its initial position by the second resilient member 170, which is defined by proximally directed surfaces of the guide ledges 28 of the distal housing part abutting the ledges 134 of the slots 132 on the release sleeve 118, FIG. 19. The user then replaces the protective cap 50, either with the medicament delivery member 102 on, or with the medicament delivery member 102 removed and discarded.

Thus, each time the user is to administer a dose of medicament the above described steps are performed. When the medicament container is almost empty, it is not possible to set a dose larger than the remaining dose. This is due to the shoulder 106 on the medicament container holder 90, because when the medicament container holder 90 is moved in the distal direction during dose setting, the shoulder 106 will be moved in contact with a proximally directed surface of the dose setting member 72, preventing any further movement of the medicament container holder 90 and thereby the medicament container 92. When the medicament container 92 is empty, the medicament delivery device 10 is discarded in a safe way.

It is to be understood that the embodiment described above and shown in the drawings is to be regarded only as a non-limiting example of the invention and that it may be modified in many ways within the scope of the patent claims.

The invention claimed is:

1. A medicament delivery device comprising a housing:
 a medicament container holder, arranged movable in relation to said housing and capable of accommodating a medicament container;
 a biased activator comprising a plunger rod, wherein the plunger rod is arranged to act on the medicament container for delivering a dose of medicament through a medicament delivery member when said biased activator is operated;
 a manually operable dose setting member operable connected to both said housing and said medicament container holder such that manual operation of said dose setting member will cause the medicament container holder with the medicament container to move towards said plunger rod for setting a dose of medicament to be delivered;
 a dose drum releasably connected to the dose setting member through a releasable connection mechanism such that when the dose setting member is operated, said dose drum is displaced from an initial position to a set dose position;
 a release mechanism operably connected to said biased activator, wherein, when said plunger rod is moved to an end position of a dose delivery operation, said release mechanism is arranged to act on said connection mechanism for releasing said dose drum from said dose setting member;
 characterised in that said release mechanism is arranged with a locking mechanism arranged to lock said dose setting member from displacement as the connection mechanism is operated for releasing said dose drum from said dose setting member.

2. The medicament delivery device according to claim 1, further comprising a first resilient member arranged between the dose drum and the housing.

3. The medicament delivery device according to claim 2, wherein the first resilient member is tensioned when the dose setting member is operated such that the dose drum is displaced from the initial position to the set dose position.

4. The medicament delivery device according to claim 3, wherein the first resilient member is capable of moving the dose drum back from the set dose position to the initial position when the dose drum is released from the dose setting member.

5. The medicament delivery device according to claim 1, wherein the connection mechanism comprises at least one resiliently arranged protrusion on the dose setting member engageable with at least one cut-out on said dose drum.

6. The medicament delivery device according to claim 1, wherein the connection mechanism comprises at least one resiliently arranged protrusion on one of the dose drum engageable with at least one cut-out on said dose setting member.

7. The medicament delivery device according to claim 1, wherein the release mechanism comprises a release sleeve.

8. The medicament delivery device according to claim 7, wherein the locking mechanism comprises at least one resiliently arranged protrusion on one of the dose setting member or the release sleeve engageable with at least one cut-out on the other of the release sleeve or the dose setting member.

9. The medicament delivery device according to claim 8, wherein the dose setting member comprises at least one arm resiliently movable in a longitudinal direction of the medicament delivery device.

10. The medicament delivery device according to claim 9, wherein the at least one arm is arranged with a protrusion arranged to engage in a cut-out of said dose drum to create the connection mechanism.

11. The medicament delivery device according to claim 10, wherein the at least one arm is arranged with a protrusion arranged to engage in a cut-out in the release sleeve for creating the locking mechanism.

12. The medicament delivery device according to claim 1, wherein the release mechanism further comprises rotational locking elements arranged to lock the dose drum and the dose setting member during delivery of the dose.

13. The medicament delivery device according to claim 1, wherein the dose setting member comprises a locking element configured to interact with a corresponding locking element of the housing for releasably locking rotational positions of the dose setting member during setting of a dose and for providing tactile and audible information during setting of the dose.

14. The medicament delivery device according to claim 13,
wherein the locking element is a recess on an outer surface of the dose setting member and the corresponding locking element is a protrusion on an inner surface of the housing.

15. The medicament delivery device according to claim 1, further comprising a dose limiting mechanism operably arranged between the dose drum and the housing, capable of limiting the maximum dose to be set.

16. Medicament delivery device according to claim 15, wherein said dose limiting mechanism comprises a groove extending a distance along a circumference of said dose drum arranged to interact with a stop ledge on said housing, wherein the turning of the dose setting member will bring the stop ledge in contact with an end of said groove within one turn of the dose setting member, limiting the maximum dose to be set.

17. Medicament delivery device according to claim 1, further comprising a last dose mechanism operably arranged between the medicament container holder and said dose setting member and capable of limiting the maximum dose to be set to the remaining quantity of medicament in the medicament container.

18. The medicament delivery device according to claim 17,
wherein the last dose mechanism comprises a stop ledge in a proximal area of the medicament container holder, arranged to come in contact with, and limit the movement, of the dose setting member.

19. The medicament delivery device according to claim 1,
wherein the biased activator comprises a manually operable push button extending in a distal direction through the housing.

20. The medicament delivery device according to claim 19,
wherein the biased activator comprises a return force element arranged to return the biased activator after delivery of a dose medicament.

* * * * *